US008989846B2

(12) United States Patent
Kuduvalli et al.

(10) Patent No.: US 8,989,846 B2
(45) Date of Patent: Mar. 24, 2015

(54) RADIATION TREATMENT DELIVERY SYSTEM WITH OUTWARDLY MOVABLE RADIATION TREATMENT HEAD EXTENDING FROM RING GANTRY

(75) Inventors: Gopinath Kuduvalli, San Jose, CA (US); Paul D. Treas, Livermore, CA (US); Adam J. Weber, San Jose, CA (US)

(73) Assignee: Accuray Incorporated, Sunnyvale, CA (US)

( * ) Notice: Subject to any disclaimer, the term of this patent is extended or adjusted under 35 U.S.C. 154(b) by 898 days.

(21) Appl. No.: 13/205,576

(22) Filed: Aug. 8, 2011

(65) Prior Publication Data

US 2012/0035470 A1 Feb. 9, 2012

Related U.S. Application Data

(60) Provisional application No. 61/371,737, filed on Aug. 8, 2010.

(51) Int. Cl.
*A61B 6/00* (2006.01)
*A61N 5/10* (2006.01)
(Continued)

(52) U.S. Cl.
CPC .................. *A61B 6/00* (2013.01); *A61B 6/4435* (2013.01); *A61B 6/4452* (2013.01); *A61B 6/4458* (2013.01); *A61B 6/4476* (2013.01); *A61N 5/10* (2013.01); *A61B 6/025* (2013.01); *A61B 6/035* (2013.01)
USPC ............. 600/427; 600/425; 600/407; 378/62; 378/64; 378/181; 378/198

(58) Field of Classification Search
None
See application file for complete search history.

(56) References Cited

U.S. PATENT DOCUMENTS

| 5,724,400 A | 3/1998 | Swerdloff et al. |
| 6,865,254 B2 | 3/2005 | Nafstadius |

(Continued)

FOREIGN PATENT DOCUMENTS

| WO | WO 2010/047923 | 4/2010 |
| WO | WO 2010/086706 | 8/2010 |

OTHER PUBLICATIONS

International Search Resort PCT/US2011/046967 mailed Dec. 9, 2011, 4 pgs.

(Continued)

*Primary Examiner* — Long V Le
*Assistant Examiner* — Bradley Impink
(74) *Attorney, Agent, or Firm* — Lowenstein Sandler LLP

(57) ABSTRACT

Systems, methods, and related computer program products for image-guided radiation treatment (IGRT) are described. For one preferred embodiment, an IGRT apparatus is provided comprising a gantry frame including a ring member, the ring member being rotatable around a substantially horizontal, longitudinally extending central axis, the ring member having first and second horizontally opposing ends. The IGRT apparatus further comprises a radiation treatment head coupled to the ring member by an arm member, the arm member being connected to the ring member at an arm member base. Preferably, the IGRT apparatus is further characterized in that the arm member extends outwardly from the first end of the ring member in a direction away from the second end and is supported only by the arm member base, and the radiation treatment head is dynamically movable in at least a longitudinal direction toward and away from the first end of the ring member.

21 Claims, 15 Drawing Sheets

(51) Int. Cl.
*A61B 6/02* (2006.01)
*A61B 6/03* (2006.01)

(56) References Cited

U.S. PATENT DOCUMENTS

| | | |
|---|---|---|
| 6,969,194 B1 | 11/2005 | Nafstadius |
| 6,977,987 B2 | 12/2005 | Yamashita et al. |
| 7,085,347 B2 | 8/2006 | Milhara et al. |
| 7,188,999 B2 | 3/2007 | Milhara et al. |
| 7,227,925 B1 | 6/2007 | Mansfield et al. |
| 7,239,684 B2 | 7/2007 | Hara et al. |
| 7,402,819 B2 * | 7/2008 | Saracen ............ 250/492.1 |
| 7,640,607 B2 | 1/2010 | Guertin et al. |
| 7,657,304 B2 | 2/2010 | Mansfield et al. |
| 7,679,073 B2 | 3/2010 | Urano et al. |
| 7,898,192 B2 | 3/2011 | Maltz |
| 7,983,380 B2 | 7/2011 | Guertin et al. |
| 2003/0048868 A1 | 3/2003 | Bailey et al. |
| 2005/0226377 A1 * | 10/2005 | Wong et al. ............ 378/65 |
| 2006/0173294 A1 | 8/2006 | Ein-Gal |
| 2006/0193435 A1 | 8/2006 | Hara et al. |
| 2007/0003010 A1 | 1/2007 | Guertin et al. |
| 2007/0014391 A1 | 1/2007 | Mostafavi et al. |
| 2007/0055144 A1 * | 3/2007 | Neustadter et al. ....... 600/425 |
| 2007/0110289 A1 * | 5/2007 | Fu et al. ............ 382/128 |
| 2007/0280408 A1 * | 12/2007 | Zhang ............ 378/10 |
| 2008/0002811 A1 * | 1/2008 | Allison ............ 378/65 |
| 2008/0071420 A1 | 3/2008 | Guertin et al. |
| 2009/0067579 A1 | 3/2009 | Mansfield |
| 2010/0020919 A1 | 1/2010 | Dragan et al. |
| 2010/0061509 A1 | 3/2010 | D'Ambrosio et al. |
| 2010/0193698 A1 | 8/2010 | Hassan |
| 2010/0296626 A1 * | 11/2010 | Hibino et al. ............ 378/44 |
| 2010/0303205 A1 * | 12/2010 | Kapoor et al. ............ 378/65 |
| 2011/0210261 A1 * | 9/2011 | Maurer, Jr. ............ 250/393 |
| 2011/0313231 A1 | 12/2011 | Guertin et al. |
| 2012/0294424 A1 * | 11/2012 | Chin et al. ............ 378/65 |

OTHER PUBLICATIONS

Kilby et al., "The CyberKnife® Robotic Radiosurgery System in 2010", Tech. in Cancer Res. and Treatment vol. 9, No. 5, pp. 433-452 (2010).

Beavis "Is tomotherapy the future of IMRT?", The British J. of Radiology 77, pp. 285-295 (2004).

Court et al., "Evaluation of mechanical precision and alignment uncertainties for an itegrated CT/LINAC system", Med. Phys. vol. 30, No. 6, pp. 1198-1210 (2003).

Jaffray et al. "Flat-panel cone-beam computed tomography for image-guided radiation therapy", Int. J. Rad. Oncology Biol. Phys. vol. 53, No. 5, pp. 1337-1349 (2002).

Kuriyama et al., "A new irradiation unit constructed of self-moving gantry-CT and LINAC", Int. J. Rad. Oncology Biol. Phys. vol. 55, No. 2, pp. 428-435 (2003).

Mackie et al., "Image guidance for precise conformal radiogtherapy", Int. J. Radiation Oncology Biol. Phys. vol. 56, No. 1, pp. 89-105 (2003).

Raaymakers et al., "Integrating a MRI scanner with a 6 MV radiotherapy accelerator: dose deposition in a transverse magnetic field", Phys. Med. Biol. vol. 49, pp. 4109-1418 (2004).

Uematsu et al., "A dual computed tomography linear accelerator unit for stereotactic radiation therapy: a new approach without cranially fixated stereotactic frames", Int. J. Rad. Oncology Biol. Phys. vol. 35, No. 3, pp. 587-592 (1996).

* cited by examiner

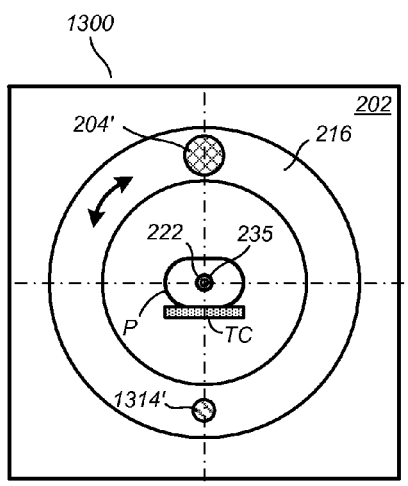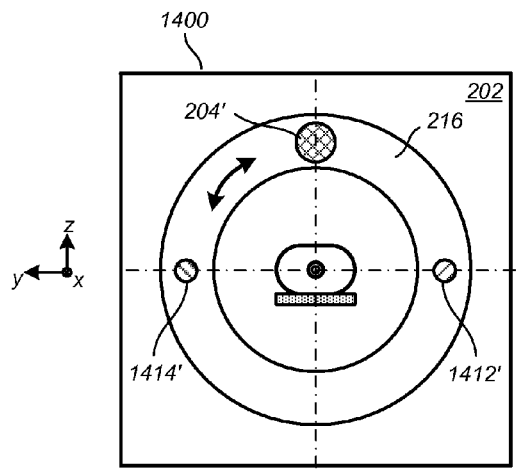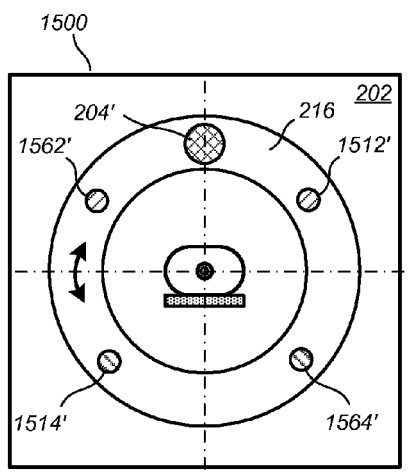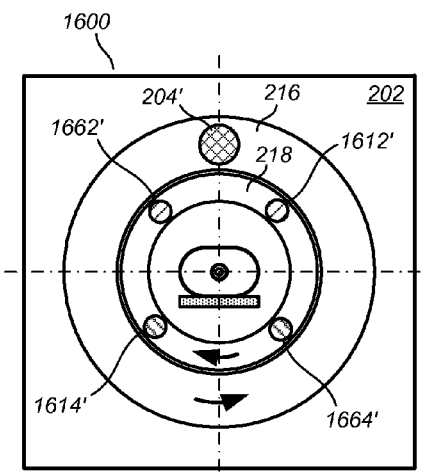
FIG. 13          FIG. 14
FIG. 15          FIG. 16

RADIATION TREATMENT DELIVERY SYSTEM WITH OUTWARDLY MOVABLE RADIATION TREATMENT HEAD EXTENDING FROM RING GANTRY

CROSS-REFERENCE TO RELATED APPLICATIONS

This application claims the benefit of U.S. Provisional Ser. No. 61/371,737 filed Aug. 8, 2010, which is incorporated by reference herein. The subject matter of this patent specification relates generally to the subject matter of U.S. Ser. No. 13/033,584, filed Feb. 23, 2011, and U.S. Ser. No. 13/156,285 filed Jun. 8, 2011, each of which is incorporated by reference herein.

FIELD

This patent specification relates to the use of radiation for medical treatment purposes. More particularly, this provisional patent specification relates to radiation treatment systems.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a therapeutic radiation source, such as a linear accelerator (LINAC), to generate radiation beams, such as x-rays. In one type of external beam radiation therapy, a therapeutic radiation source directs a sequence of x-ray beams at a tumor site from multiple coplanar angles, with the patient positioned so the tumor is at the center of rotation (isocenter) of the beam. As the angle of the therapeutic radiation source changes, every beam passes through the tumor site, but passes through a different area of healthy tissue on its way to and from the tumor. As a result, the cumulative radiation dose at the tumor is high and that to healthy tissue is relatively low.

The term "radiosurgery" refers to a procedure in which radiation is applied to a target region at doses sufficient to necrotize a pathology in fewer treatment sessions or fractions than with delivery of lower doses per fraction in a larger number of fractions. Radiosurgery is typically characterized, as distinguished from radiotherapy, by relatively high radiation doses per fraction (e.g., 500-2000 centiGray), extended treatment times per fraction (e.g., 30-60 minutes per treatment), and hypo-fractionation (e.g., one to five fractions or treatment days). Radiotherapy is typically characterized by a low dose per fraction (e.g., 100-200 centiGray), shorter fraction times (e.g., 10 to 30 minutes per treatment) and hyperfractionation (e.g., 30 to 45 fractions). For convenience, the term "radiation treatment" is used herein to mean radiosurgery and/or radiotherapy unless otherwise noted.

Image-guided radiation therapy (IGRT) systems include gantry-based systems and robotic arm-based systems. In gantry-based systems, a gantry rotates the therapeutic radiation source around an axis passing through the isocenter. Gantry-based systems include C-arm gantries, in which the therapeutic radiation source is mounted, in a cantilever-like manner, over and rotates about the axis passing through the isocenter. Gantry-based systems further include ring gantries having generally toroidal shapes in which the patient's body extends through a bore of the ring/toroid, and the therapeutic radiation source is mounted on the perimeter of the ring and rotates about the axis passing through the isocenter. Traditional gantry systems (ring or C-arm) deliver therapeutic radiation in single plane (i.e., co-planar) defined by the rotational trajectory of the radiation source. Examples of C-arm systems are manufactured by Siemens of Germany and Varian Medical Systems of California. In robotic arm-based systems, the therapeutic radiation source is mounted on an articulated robotic arm that extends over and around the patient, the robotic arm being configured to provide at least five degrees of freedom. Robotic arm-based systems provide the capability to deliver therapeutic radiation from multiple out-of-plane directions, i.e., are capable of non-coplanar delivery. Accuray Incorporated of California manufactures a system with a radiation source mounted on a robotic arm for non-coplanar delivery of radiation beams.

Associated with each radiation therapy system is an imaging system to provide in-treatment images that are used to set up and, in some examples, guide the radiation delivery procedure and track in-treatment target motion. Portal imaging systems place a detector opposite the therapeutic source itself to image the patient for setup and in-treatment images, while other approaches utilize distinct, independent image radiation source(s) and detector(s) for the patient set-up and in-treatment images. Target or target volume tracking during treatment is accomplished by comparing in-treatment images to pre-treatment image information. Pre-treatment image information may comprise, for example, computed tomography (CT) data, cone-beam CT data, magnetic resonance imaging (MRI) data, positron emission tomography (PET) data or 3D rotational angiography (3DRA) data, and any information obtained from these imaging modalities (for example and without limitation digitally reconstructed radiographs or DRRs).

In one common scenario, the therapeutic source is a linear accelerator (LINAC) producing therapeutic radiation (which can be termed an "MV source") and the imaging system comprises one or more independent x-ray imaging sources producing relatively low intensity, lower energy imaging radiation (each of which can be termed a "kV source"). In-treatment images can comprise one or more (preferably two) two-dimensional images (typically x-ray) acquired at one or more different points of view (e.g., stereoscopic x-ray images), and are compared with two-dimensional DRRs derived from the three dimensional pre-treatment image information. A DRR is a synthetic x-ray image generated by casting rays through the 3D imaging data, where the rays simulate the geometry of the in-treatment x-ray imaging system. The resulting DRR then has approximately the same scale and point of view as the in-treatment x-ray imaging system, and can be compared with the in-treatment x-ray images to determine the position and orientation of the target, which is then used to guide delivery of radiation to the target.

There are two general goals in radiation therapy: (i) to deliver a highly conformal dose distribution to the target volume; and (ii) to deliver treatment beams with high accuracy throughout every treatment fraction. A third goal is to accomplish the two general goals in as little time per fraction as possible. Delivering a conformal dose distribution requires, for example, the ability to deliver non-coplanar beams. Delivering treatment beams accurately requires the ability to track the location of the target volume. The ability to increase delivery speed requires the ability to accurately and precisely move the radiation source without hitting other objects in the room or the patient.

One or more issues arise with respect to known radiation therapy systems that are at least partially addressed by one or more of the preferred embodiments described further hereinbelow. Generally speaking, these issues relate to less than optimal trade-offs and compromises in both functionality and patient experience presented by and among known robot arm-based systems and gantry-based systems. By way of example, the rotational trajectories of known ring gantry-based systems tend to provide for good mechanical stability and relatively high mechanical drive speeds, but tend to be less versatile in the kinds of therapy plans that can be provided, such as an inability to provide apex-oriented radiation beams for cranial treatments and non-coplanar radiation treatment delivery. On the other hand, known robot arm-based systems tend to provide high versatility and a wide range of radiation treatment profiles, including apex-oriented radiation beams for cranial treatments and non-coplanar radiation treatment delivery, but tend to require longer times per treatment fraction due to the limited speeds at which the robot arm can manipulate the radiation treatment head. Other issues arise as would be apparent to a person skilled in the art in view of the present teachings.

SUMMARY

Provided according to one preferred embodiment is an image-guided radiation treatment (IGRT) apparatus comprising a gantry frame including a ring member, the ring member being rotatable around a substantially horizontal, longitudinally extending central axis. The ring member has first and second horizontally opposing ends. The IGRT apparatus further comprises a radiation treatment head coupled to the ring member in an outwardly movable manner by an arm member extending outwardly from the first end of the ring member in a direction away from the second end. The outward movability of the radiation treatment head is characterized in that the radiation treatment head is movable in at least a longitudinal direction toward and away from the first end of the ring member.

Also provided is a method for image guided radiation treatment of a body part of a patient. The patient is positioned into a treatment position relative to an IGRT apparatus that comprises a gantry frame including a ring member, the ring member being rotatable around a substantially horizontal, longitudinally extending central axis and having first and second horizontally opposing ends, the IGRT apparatus further comprising a radiation treatment head coupled to the ring member in an outwardly movable manner by an arm member extending outwardly from the first end of the ring member in a direction away from the second end, the outward movability being characterized in that the radiation treatment head is movable in at least a longitudinal direction toward and away from the first end of the ring member. The method further comprises operating the IGRT apparatus to apply non-coplanar radiation treatment to the body part during a treatment fraction, the operating comprising rotating the ring member to a plurality of different gantry angles to move the radiation treatment head to a corresponding plurality of different treatment angles. The operation of the IGRT apparatus further comprises moving the radiation treatment head to a plurality of different outward distances from the first end of the ring member.

Also provided is an IGRT apparatus comprising a gantry frame including a ring member, the ring member being rotatable around a substantially horizontal, longitudinally extending central axis, the ring member having first and second horizontally opposing ends. The IGRT apparatus further comprises a radiation treatment head coupled to the ring member by an arm member, the arm member being connected to the ring member at an arm member base. Preferably, the IGRT apparatus is further characterized in that the arm member extends outwardly from the first end of the ring member in a direction away from the second end and is supported only by the arm member base, and the radiation treatment head is dynamically movable in at least a longitudinal direction toward and away from the first end of the ring member.

BRIEF DESCRIPTION OF THE DRAWINGS

FIGS. 13-16 illustrate endwise cutaway views of examples of different IGRT apparatuses according to one or more preferred embodiments;

DETAILED DESCRIPTION

Figure 1:
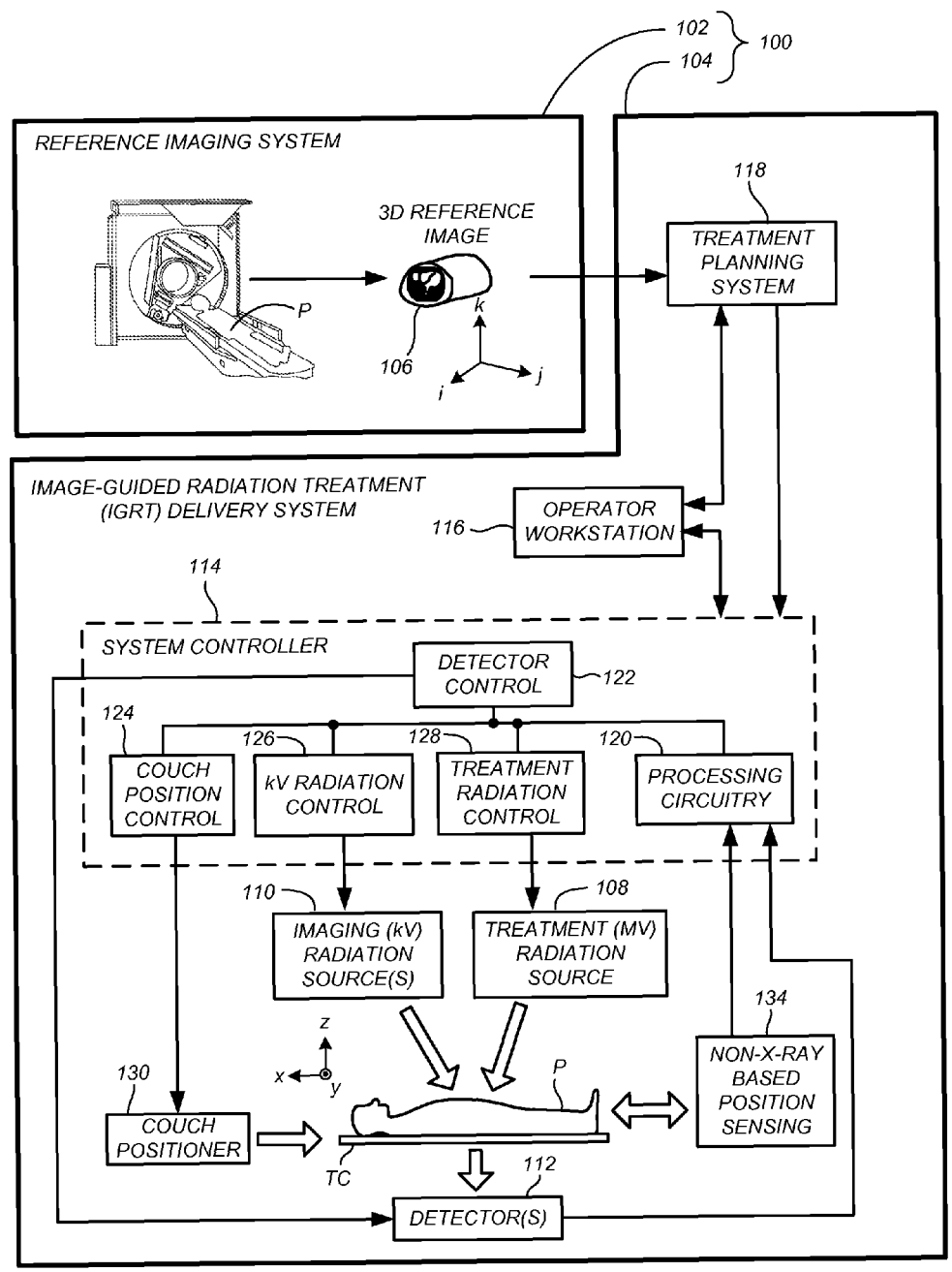
FIG. 1 illustrates a radiation treatment environment according to a preferred embodiment.

FIG. 1 illustrates a radiation treatment environment 100 within which one or more of the preferred embodiments is advantageously applied. The radiation treatment environment 100 includes a reference imaging system 102 and an IGRT system 104. Reference imaging system 102 usually comprises a high precision volumetric imaging system such as a computed tomography (CT) system or a nuclear magnetic resonance imaging (MRI) system. In view of cost and workflow considerations in many clinical environments, the reference imaging system 102 is often a general purpose tool used for a variety of different purposes in the clinic or hospital environment, and is not specifically dedicated to the IGRT system 104. Rather, the reference imaging system 102 is often located in its own separate room or vault and is purchased, installed, and/or maintained on a separate and more generalized basis than the IGRT system 104. Accordingly, for the example of FIG. 1, the reference imaging system 102 is illustrated as being distinct from the IGRT system 104.

Notably, for other radiation treatment environments that are not outside the scope of the present teachings, the reference imaging system 102 can be considered as an integral component of the IGRT system 104. By way of example, for one preferred embodiment illustrated in FIGS. 18A-18D infra, the reference imaging system 102 and IGRT system 104 can take the form of a CT imaging system 1851 that forms a common central bore 1820 with a ring member 1816 of an IGRT system 1801 in which a radiation treatment head 1806 extends outwardly from the ring member 1816 by an articulated robotic arm 1804. Such physical integration or co-location of a high resolution CT imaging system with an IGRT system can advantageously facilitate improved registration of intrafraction images acquired by the onboard imaging hardware of the IGRT system with the high resolution three-dimensional CT images acquired by the high resolution CT imaging system.

Referring now again to FIG. 1, IGRT system 104 comprises a radiation treatment (MV) source 108 that selectively applies high-energy x-ray treatment radiation to a target volume of a patient P positioned on a treatment couch TC. The MV source 108 applies the treatment radiation under the control of a system controller 114, and more particularly a treatment radiation control subsystem 128 thereof. System controller 114 further comprises processing circuitry 120, a detector controller 122, a couch position controller 124, and a kV radiation controller 126. One or more imaging (kV) radiation sources 110 selectively emit relatively low-energy x-ray imaging radiation under the control of kV radiation controller 126, the imaging radiation being captured by one or more imaging detectors 112. In alternative preferred embodiments, one or more of the imaging detectors 112 can be a so-called portal imaging detector that captures high-energy x-ray treatment radiation from MV source 108 that has propagated through the target volume.

For one preferred embodiment, the kV imaging radiation sources 110 include both a two-dimensional stereotactic x-ray imaging system and a tomosynthesis imaging system. For other preferred embodiments, only a two-dimensional stereotactic x-ray imaging system is provided, while for still other preferred embodiments only a tomosynthesis imaging system is provided. Preferably, each of the stereotactic x-ray imaging system and the tomosynthesis imaging system are characterized by either (a) a fixed, predetermined, nonmoving geometry relative to the (x, y, z) coordinate system of the treatment room, or (b) a precisely measurable and/or precisely determinable geometry relative to the (x, y, z) coordinate system of the treatment room in the event they are dynamically moveable. The MV radiation source 108 should also, of course, have a precisely measurable and/or precisely determinable geometry relative to the (x, y, z) coordinate system of the treatment room.

A couch positioner 130 is actuated by the couch position controller 124 to position the couch TC. Optionally, a non-x-ray based position sensing system 134 senses position and/or movement of external marker(s) strategically affixed to the patient, and/or senses position and/or movement of the patient skin surface itself, using one or more methods that do not involve ionizing radiation, such as optically based or ultrasonically based methods. IGRT system 104 further includes an operator workstation 116 and a treatment planning system 118.

Figure 2A:
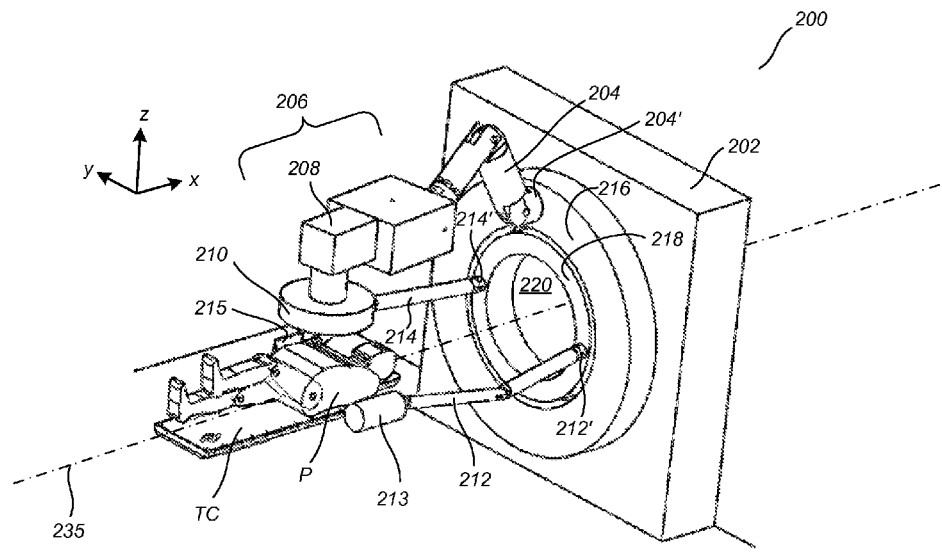
FIG. 2A illustrates a perspective view of an image-guided radiation treatment (IGRT) apparatus according to a preferred embodiment.

FIG. 2A illustrates a perspective view of an IGRT system 200 according to a preferred embodiment. The IGRT system 200 of FIG. 2A is further illustrated and described with respect to FIG. 2B which shows an endwise cutaway view of the IGRT apparatus 200, FIG. 3 which shows a side view of an articulated robot arm 204 of the IGRT apparatus 200, and FIG. 4 which shows a side view of the IGRT apparatus 200 and a schematic diagram of a computer system integral therewith and/or coupled thereto. IGRT system 200 comprises a gantry frame 202 including a first ring member 216, the first ring member 216 being rotatable around a substantially horizontal, longitudinally extending central axis 235. The first ring member 216 has a first end 216F (see FIG. 4) and second end 216B (see FIG. 4) that horizontally opposes the first end 216F. The IGRT apparatus 200 further comprises a radiation treatment head 206 coupled to the first ring member 216 in an outwardly movable manner by an arm member 204 that extends in an outward direction relative to the first ring member 216. By outward direction, it is meant that the arm member 204 extends laterally over locations that are not laterally occupied by the first ring member 216, that is, the arm member 204 extends from the first end 216F in a direction pointing away from the second end 216B. The outward movability of the radiation treatment head 206 is characterized in that the radiation treatment head 206 is movable in at least a longitudinal direction toward and away from the first end 216F of the ring member.

Figure 2B:
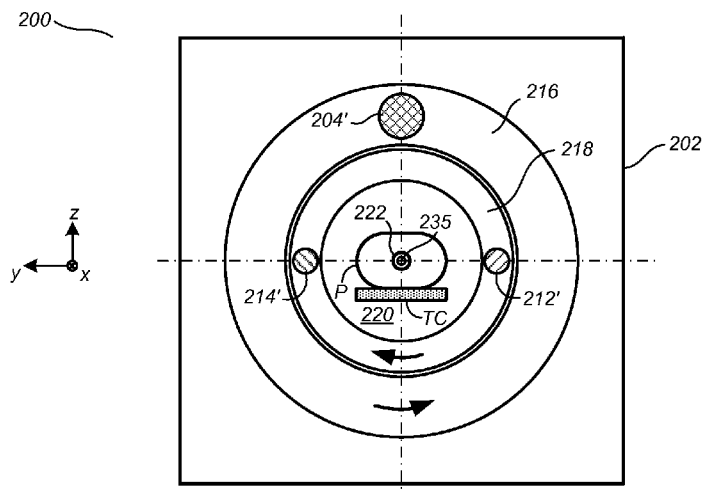
FIG. 2B illustrates an endwise cutaway view of the IGRT apparatus of FIG. 2A.

According to the preferred embodiment of FIGS. 2A-2B, the arm member 204 is an articulated robot arm having a shoulder joint 204' connected to the first ring member 216, the radiation treatment head 206 being coupled to the articulated robot arm 204 at a distal end thereof opposite the shoulder joint 204'. While the use of an articulated robot arm has been found to be particularly advantageous in providing a highly versatile range of positions and orientations for the radiation treatment head 206, it is to be appreciated that the scope of the present teachings is not so limited. By way of example, in other preferred embodiments (see FIGS. 17A-17B infra) the radiation treatment head may be slidably and tiltably coupled to a single continuous beam member that extends outwardly from the ring member at a fixed orientation.

Referring now again to FIGS. 2A-2B, the radiation treatment head 206 includes a collimator 210, such as a multi-leaf collimator (MLC), and preferably includes a bending magnet 208, such as a 270-degree or 90-degree bending magnet. The use of bending magnet 208 promotes physical compactness in a radial dimension around the central axis 235, which is particularly useful in accommodating radiation treatment delivery angles from underneath the treatment couch TC (see FIG. 9 and FIG. 12, infra) without requiring the treatment couch TC to be too far above the floor of the treatment room.

Shown in FIG. 2B is an endwise cutaway view of the IGRT apparatus 200 when viewed in the positive-x direction at a hypothetical cut plane (not shown) that is parallel to the y-z plane and immediately next to the first end 216F of the first ring member 216 on the negative-x side thereof. The endwise cutaway view of FIG. 2B, for which the particular structure of the outwardly extending arms is thereby not shown, is provided for clarity in presenting the number and locations of arm members extending from the first ring member 216 and a second ring member 218. According to a preferred embodiment, the gantry frame 202 further includes a second ring member 218 that is rotatable around the central axis 235 independently of the first ring member, a kV imaging source 213 coupled to the second ring member 218 in an outwardly movable manner by an arm member 212, and a kV imaging detector 215 coupled to the second ring member 218 in an outwardly movable manner by an arm member 214, the arm members 212 and 214 being generally opposite each other relative to the central axis 235.

For the preferred embodiment of FIGS. 2A-2B, the second ring member 218 is an inner ring member relative to the first ring member 216 and defines a central bore 220. The scope of the present teachings is not so limited, however, and further encompasses alternative scenarios in which the second ring member supporting the kV imaging equipment lies outside the first ring member supporting the radiation treatment head relative to the central axis.

According to the preferred embodiment of FIGS. 2A-2B, each of the respective arm members 212 and 214 is an articulated robot arm having a respective shoulder joint 212' and 214' connected to the second ring member 218, the kV imaging source 213 and kV imaging detector 215 being coupled to the respective articulated robot arms 212 and 214 at respective distal ends thereof. While the use of articulated robot arms has been found to be particularly advantageous in providing a highly versatile range of positions and orientations for the kV imaging source 213 and kV imaging detector 215, it is to be appreciated that the scope of the present teachings is not so limited. By way of example, in other preferred embodiments (see FIGS. 17A-17B infra), each of the kV imaging source and kV imaging detector may be slidably (and, optionally, tiltably) coupled to a single continuous beam member that extends outwardly at a fixed orientation.

Figure 3:
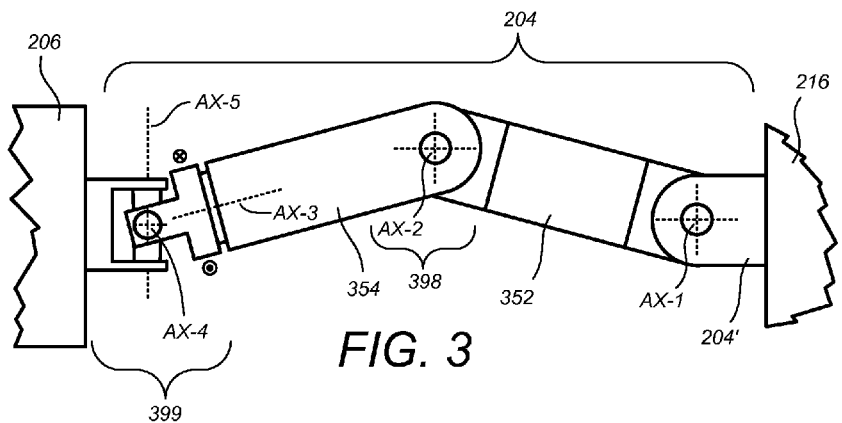
FIG. 3 illustrates a side view of an articulated robot arm of an IGRT apparatus according to a preferred embodiment.

FIG. 3 illustrates a conceptual side view of the articulated robot arm 204 as connected to the first ring member 216 at a shoulder joint 204', and to which is connected the radiation treatment head 206 at a three degree-of-freedom wrist joint 399. The articulated robot arm 204 includes a first arm segment 352 coupled between the shoulder joint 204' and an elbow joint 398, and a second arm segment 354 coupled between the elbow joint 398 and the wrist joint 399. The articulated robot arm 204 thereby provides five (5) individually controlled degrees of freedom for movement of the radiation treatment head 206, including: rotation around an axis AX-1 at shoulder joint 204'; rotation around an axis AX-2 at elbow joint 398; rotation around axis AX-3 where wrist joint 399 meets second arm segment 354; and rotation around the two axes AX-4 and AX-5 at wrist joint 399. A sixth degree of freedom for movement of the radiation treatment head 206 is provided by rotation of the first ring member 216 around the central axis 235. One or more electrical and/or pneumatic actuation devices (not shown) under computerized control, such as stepper motors and associated gearing, is provided in conjunction with each of the rotation axes AX-1, AX-2, AX-3, AX-4, and AX-5 to achieve the described movement functionality.

According to one preferred embodiment, each of the articulated robot arms 212 and 214 associated with the onboard kV imaging system is also provided five (5) individually controlled degrees of freedom in a manner similar to that of the articulated robot arm 204, with a sixth degree of freedom being provided for movement of the kV imaging system equipment by rotation of the second ring member 218 around the central axis 235. The individual components of the articulated robot arm 204 will generally need to be substantially more robust than corresponding components of the articulated robot arms 212 and 214, since the radiation treatment head 206 will generally far outweigh the kV imaging system components. Generally speaking, the articulated robot arm 204 should be sufficiently powerful and robust to manipulate the radiation treatment head 206 to an outward position that will effectively treat a patient whose entire body is positioned outwardly from the first end 216F of the first ring member 216 in the direction opposite the second end 216B. Counterweights (not shown), including but not limited to dynamically moving counterweights, are provided on the side of the gantry frame 202 opposite the radiation treatment head 206. Particular details regarding the structure and configuration of that actuation devices and counterweighting schemes necessary to implement the preferred embodiments described hereinabove and hereinbelow would be apparent to a person skilled in the art in view of the present disclosure and could be implemented using known mechanical and electromechanical technologies.

Figure 4:
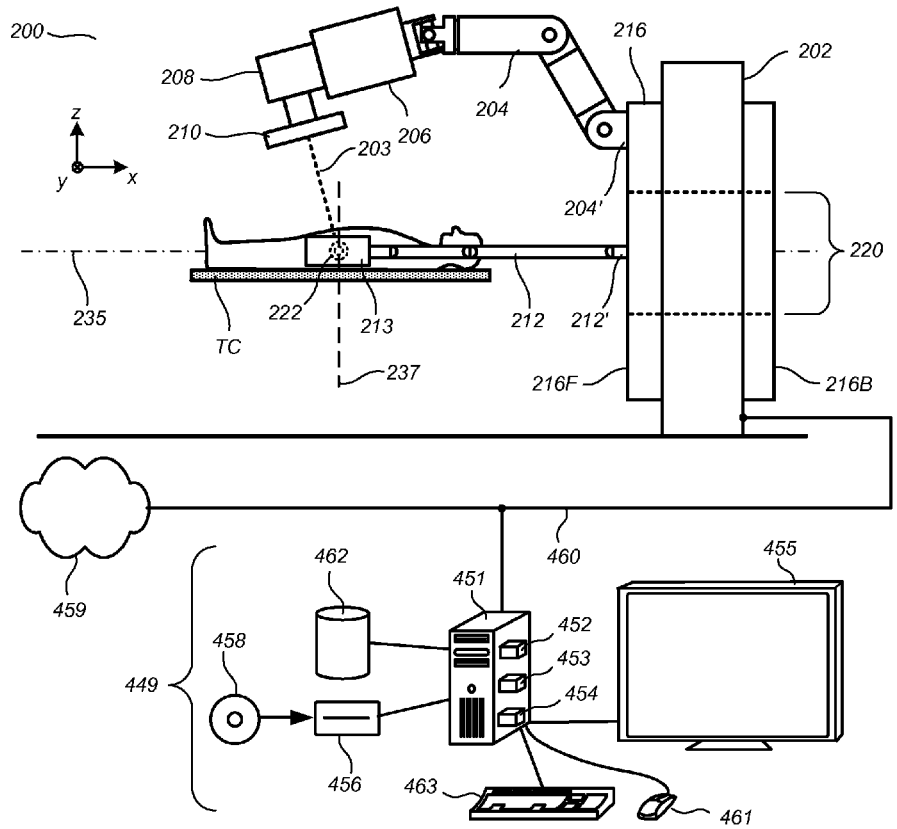
FIG. 4 illustrates a side view of an IGRT apparatus and a schematic diagram of a computer system integral therewith and/or coupled thereto according to a preferred embodiment.

FIG. 4 illustrates a side view of the IGRT apparatus 200 and a schematic diagram of a computerized control system 449 integral therewith and/or coupled thereto. Illustrated in FIG. 4 is a treatment center 222 and a transverse treatment center plane 237, the transverse treatment center plane 237 being defined as a plane normal to the central axis 235 and passing through the treatment center 222. Advantageously, the IGRT apparatus 200 can accommodate a treatment center 222 at any of a plurality of longitudinal locations along the central axis 235 by virtue of the longitudinal movability of the radiation treatment head 206. Moreover, by operation of the articulated robotic arm 204, the radiation treatment head 206 is dynamically tiltable relative to the transverse treatment center plane 237 for any of the longitudinal treatment center locations, whereby the IGRT apparatus 200 is capable of both noncoplanar radiation treatment for any of said longitudinal treatment center locations. Furthermore, also by virtue of the five degree-of-freedom robotic arm 204, the radiation treatment head 206 enjoys the equivalent of dynamic two-axis pivotability when pointed in the general direction of the treatment center, thereby readily accommodating non-isocentric (or, more generally, non-treatment center-centric) treatment as well as dynamic target tracking to accommodate intrafraction patient movement.

Further illustrated in FIG. 4 is the IGRT system 200 as coupled to and/or integrated with a computerized control system 449 using one or more busses, networks, or other communications systems 460, including wired and/or wireless communications systems, and being capable in conjunction therewith of implementing the methods of one or more of the preferred embodiments. Methods of image guided radiation treatment in accordance with one or more of the preferred embodiments may be implemented in machine readable code (i.e., software or computer program product) and performed on computer systems such as, but not limited to, the computer system 449, wherein a central processing unit (CPU) 451 including a microprocessor 452, random access memory 453, and nonvolatile memory 454 (e.g., electromechanical hard drive, solid state drive) is operated in conjunction with various input/output devices, such as a display monitor 455, a mouse 461, a keyboard 463, and other I/O devices 456 capable of reading and writing data and instructions from machine readable media 458 such as tape, compact disk (CD), digital versatile disk (DVD), blu-ray disk (BD), and so forth. In addition, there may be connections via the one or more busses, networks, or other communications systems 460 to other computers and devices, such as may exist on a network of such devices, e.g., the Internet 459. Software to control the image guided radiation treatment steps described herein may be implemented as a program product and stored on a tangible storage device such as the machine readable medium 458, an external nonvolatile memory device 462, or other tangible storage medium. For clarity of presentation, the computer system 449 of FIG. 4 is omitted from further drawings and/or descriptions hereinbelow. Methods for configuring and programming the computer system 449 for achieving the functionalities described herein would be apparent to a person skilled in the art in view of the present disclosure.

The IGRT system 200 provides a rich combination of advantageous features and capabilities, including an ability to accommodate a wide variety of radiation treatment delivery profiles (e.g., non-coplanar as well as coplanar, non-isocentric as well as isocentric) and an ability to accommodate multiple treatment centers at different longitudinal positions. Advantageously and synergistically, the IGRT system 200 combines this treatment delivery versatility with good mechanical stability and relatively high mechanical drive speeds as made achievable by its ring gantry-based rotation. The IGRT system 200 is further advantageous in that an "open" or "non-claustrophobic" feeling and experience is imparted to the patient during the treatment fraction, which is generally preferable to a "closed" or "tunnel-like" feeling and experience that can be imparted by some systems. As still another advantage, a wide variety of intrafraction imaging types and strategies can be achieved including, but not limited to, intrafraction kV stereoscopic x-ray imaging (e.g., by acquiring a first kV image and then rotating the second ring member through a stereoscopic imaging arc and then acquiring a second kV image to acquire a stereoscopic kV image pair), intrafraction tomosynthesis imaging, and intrafraction CBCT imaging, which can optionally be implemented using one or more of the advanced imaging and registration methods described in the commonly assigned Ser. No. 13/033,584, supra, and Ser. No. 13/156,285, supra. As still another advantage, in many implementations the radiation treatment head 206, kV imaging source 213, and kV imaging detector 215 can be neatly "folded away" by their robotic arms to positions close-in to the gantry frame 202, thereby allowing for more room for other activity and/or equipment in the clinical environment when the IGRT system 200 is not in use.

Figure 5:
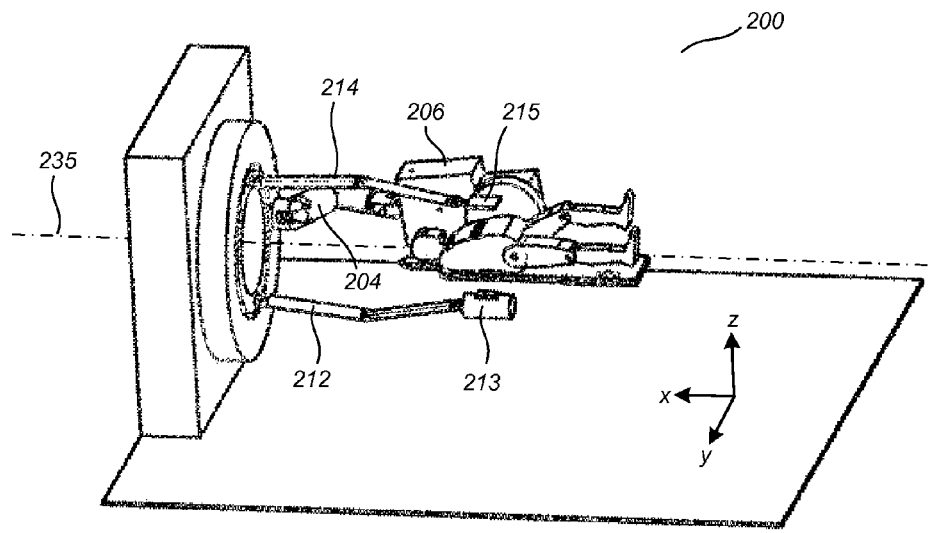
FIGS. 5-6 illustrate perspective views of the IGRT apparatus of FIG. 2A.
Figure 6:
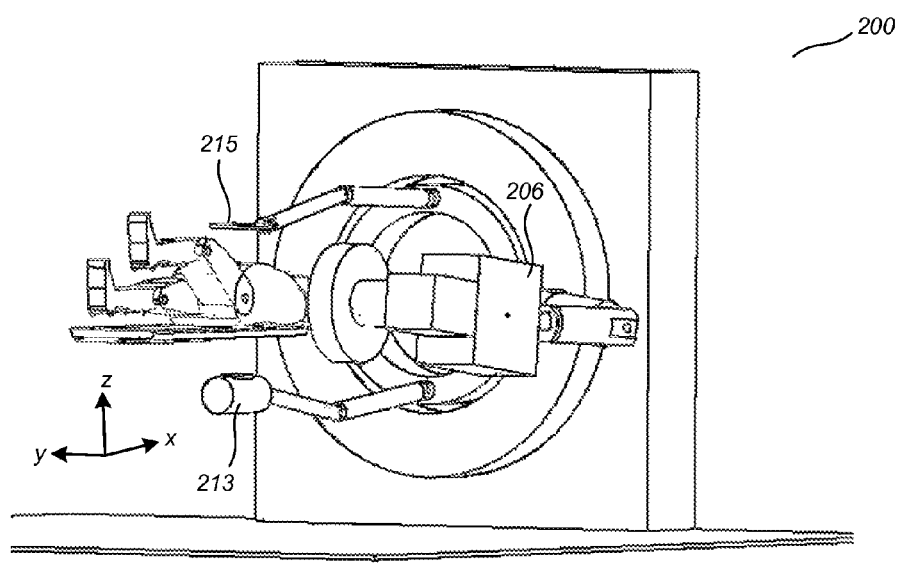

FIGS. 5-6 illustrate perspective views of the IGRT apparatus 200 at a point in time in which the radiation treatment head 206 is at the side of the patient. In the particular scenario of FIGS. 5-6, which is one of many different possible scenarios, the kV source-detector pair 213/215 is maintained at right angle to the radiation treatment beam.

Figure 7:
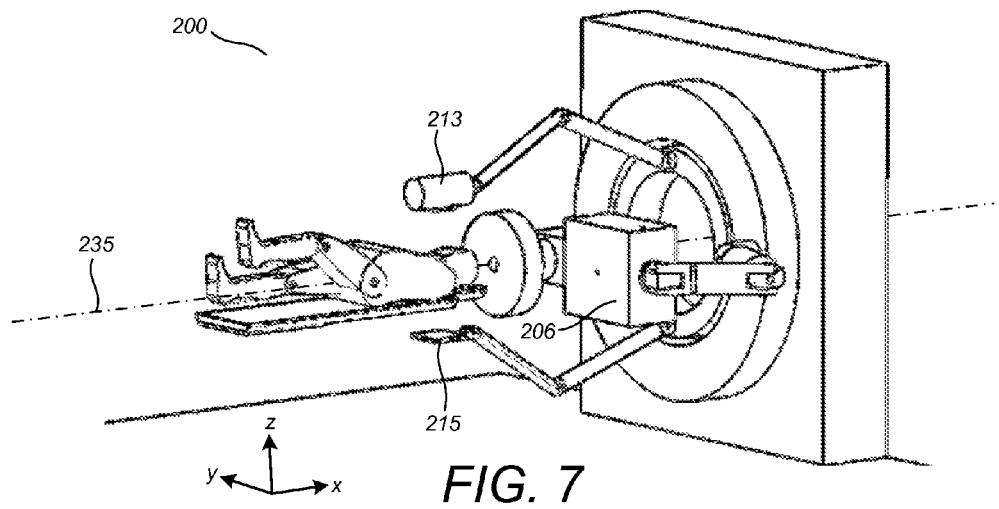
FIGS. 7-8 illustrate a perspective view and a top view, respectively, of the IGRT apparatus of FIG. 2A in an apex cranial treatment position according to a preferred embodiment.
Figure 8:
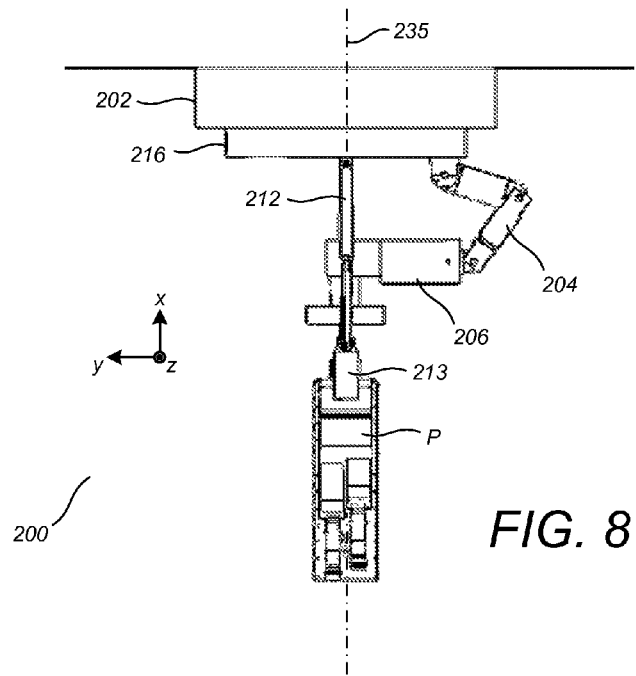

FIGS. 7-8 illustrate a perspective view and a top view, respectively, of the IGRT apparatus 200 in an apex cranial treatment position. The articulated robot arm 204 is configured such that said radiation treatment head is dynamically movable into the apex treatment position, wherein the radiation treatment beam emanates therefrom at or near the central axis 235 and is substantially parallel to the central axis 235.

Figure 9:
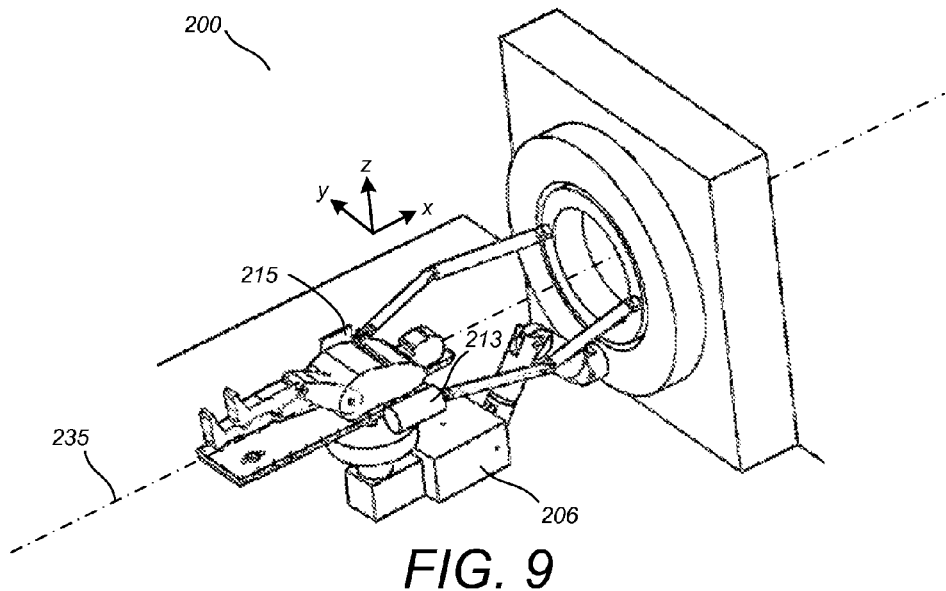
FIG. 9 illustrates a perspective view of the IGRT apparatus of FIG. 2A.
Figure 10:
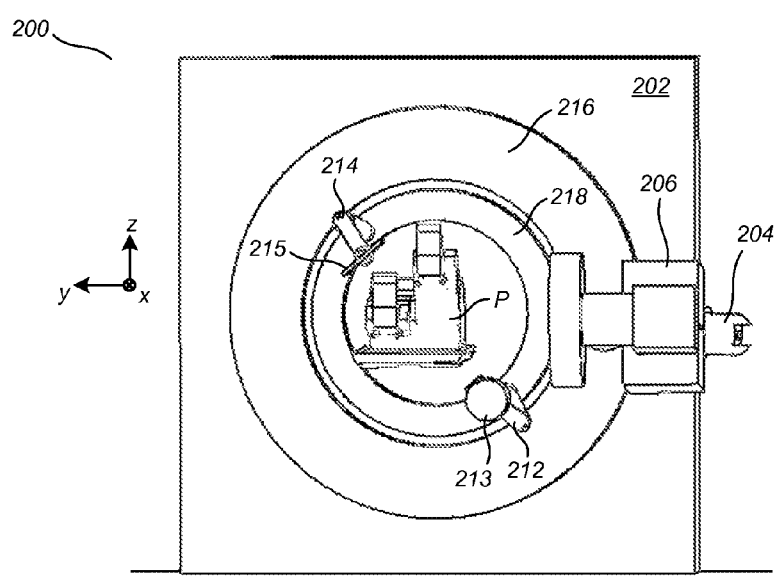
FIGS. 10-12 illustrate end views of the IGRT apparatus of FIG. 2A.
Figure 11:
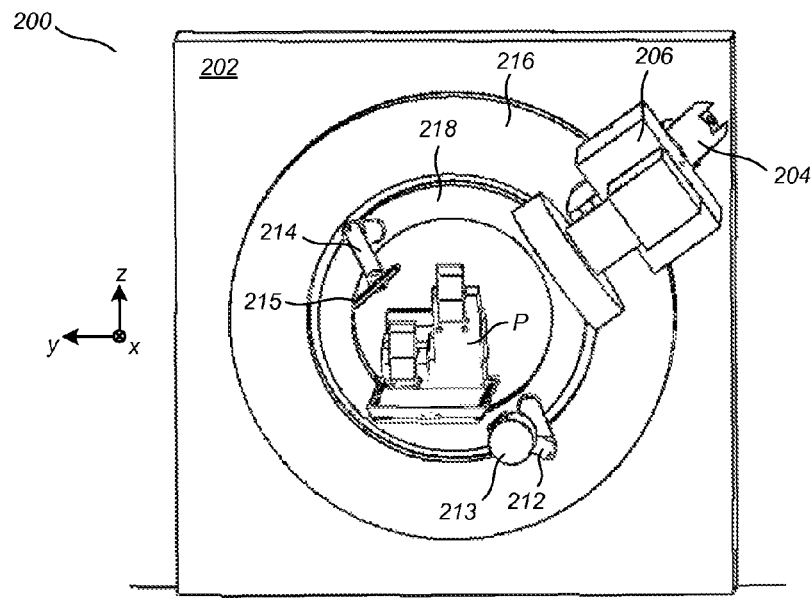
Figure 12:
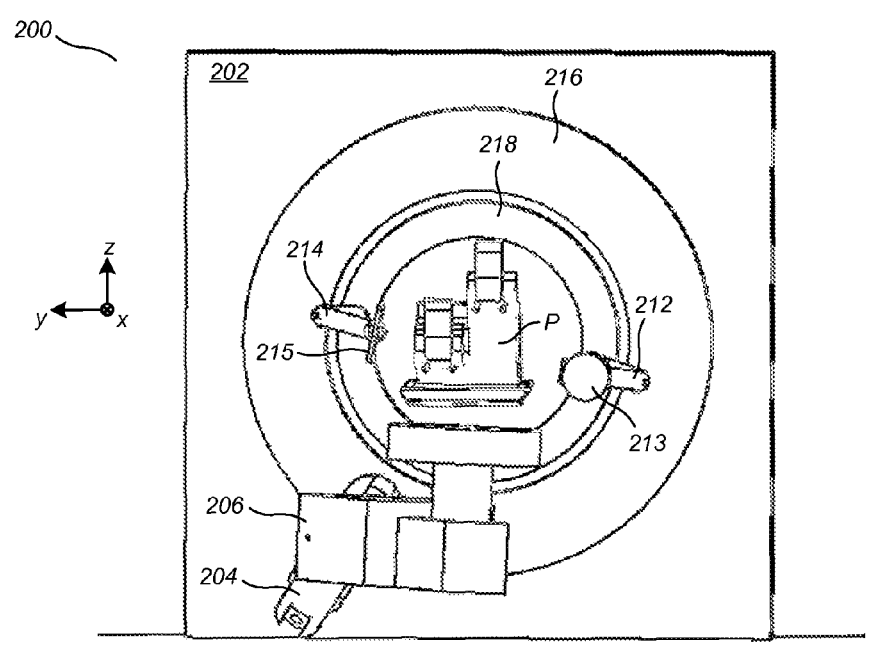

FIG. 9 illustrates a perspective view of the IGRT apparatus 200 at a point in time in which the radiation treatment head 206 is underneath the treatment couch TC. FIGS. 10-12 illustrate end views of the IGRT apparatus 200 at various rotational positions of the radiation treatment head 206 and kV source-detector pair 213/215.

FIGS. 13-16 illustrate endwise cutaway views of respective IGRT systems 1300, 1400, 1500, and 1600 which represent some of the many variations from the configuration of the IGRT system 200 of FIGS. 2A-2B that are also within the scope of the present teachings. Thus, for example, the IGRT system 1300 of FIG. 13 only contains a single ring member 216, the radiation treatment head (not shown) being coupled thereto in an outwardly movable manner by an arm member (not shown, which can be articulated or non-articulated in respective preferred embodiments) connected thereto at a shoulder 204', wherein a portal imaging detector (not shown) is coupled to that same ring member 216 in an outwardly movable manner by an arm member (not shown, which can be articulated or non-articulated in respective preferred embodiments) connected thereto at a shoulder 1314', the portal imaging detector being disposed generally opposite the radiation treatment head relative to the central axis 235 and rotating in unison therewith.

As another example, the IGRT system 1400 of FIG. 14 likewise only contains a single ring member 216, the radiation treatment head (not shown) being coupled thereto in an outwardly movable manner by an arm member (not shown, which can be articulated or non-articulated in respective preferred embodiments) connected thereto at a shoulder 204', the IGRT system 1400 further comprising a kV imaging source-detector pair (not shown) coupled to the ring member 216 in an outwardly movable manner by respective arm members (not shown, which can be articulated or non-articulated in respective preferred embodiments) connected thereto at respective shoulder joints 1412' and 1414', kV imaging source-detector pair being disposed at a generally normal angle relative to the radiation treatment beam with respect to the central axis 235 and rotating in unison with the radiation treatment head therearound.

As another example, the IGRT system 1500 of FIG. 15 likewise only contains a single ring member 216, the radiation treatment head (not shown) being coupled thereto in an outwardly movable manner by an arm member (not shown, which can be articulated or non-articulated in respective preferred embodiments) connected thereto at a shoulder 204', the IGRT system 1500 further comprising a two kV imaging source-detector pairs (not shown) coupled to the ring member 216 in an outwardly movable manner by respective arm members (not shown, which can be articulated or non-articulated in respective preferred embodiments) connected thereto at respective shoulder joints 1512', 1514', 1562', and 1564', the two kV imaging source-detector pairs being disposed at a stereoscopic imaging arc with respect to each other and rotating in unison with the radiation treatment head around the central axis 235. In yet other examples (not shown), there can be a single kV source-detector pair, or alternatively two kV source-detector pairs, coupled directly to the gantry frame 202 by arm members (which can be articulated or non-articulated in respective preferred embodiments) such that they are not rotatable at all around the central axis 235, but rather are fixed in angular position relative to the central axis 235.

As still another example, the IGRT system 1600 of FIG. 16 contains two ring members 216 and 218, the radiation treatment head (not shown) being coupled to the first ring member 216 in an outwardly movable manner by an arm member (not shown, which can be articulated or non-articulated in respective preferred embodiments) connected thereto at a shoulder 204', the IGRT system 1600 further comprising a two kV imaging source-detector pairs (not shown) coupled to the ring member 218 in an outwardly movable manner by respective arm members (not shown, which can be articulated or non-articulated in respective preferred embodiments) connected thereto at respective shoulder joints 1612', 1614', 1662', and 1664', the two kV imaging source-detector pairs being disposed at a stereoscopic imaging arc with respect to each other and rotating independently of the radiation treatment head around the central axis 235.

For many of the above-described preferred embodiments in which the kV imaging source-detector pairs are coupled to a second ring member rotatable around the central axis independently of a first ring member to which the radiation treatment head is connected, it is preferable according to some implementations to electrically connect the kV imaging source-detector pairs to external kV imaging driving circuitry through slip-ring electrical contacts (not shown) included in the second ring member. The use of the slip-ring electrical contacts allows the second ring member to rotate continuously through multiple rotations in a single rotational direction, for providing versatility in the kinds of intrafraction imaging trajectories (e.g., tomosynthesis imaging arc, CBCT imaging arcs) that can be provided. Generally speaking, for practical reasons relating to the large amount of electrical power required by LINACs, the radiation treatment head will most often be connected to external LINAC driving circuitry by standard electrical cabling rather than through slip rings. However, it is not necessarily outside the scope of the present teachings to provide slip-ring or slip-ring-like electrical contact between the LINAC and the external LINAC driving circuitry, which would thereby permit multiple rotations of the LINAC in a single rotational direction as well.

Figure 17A:
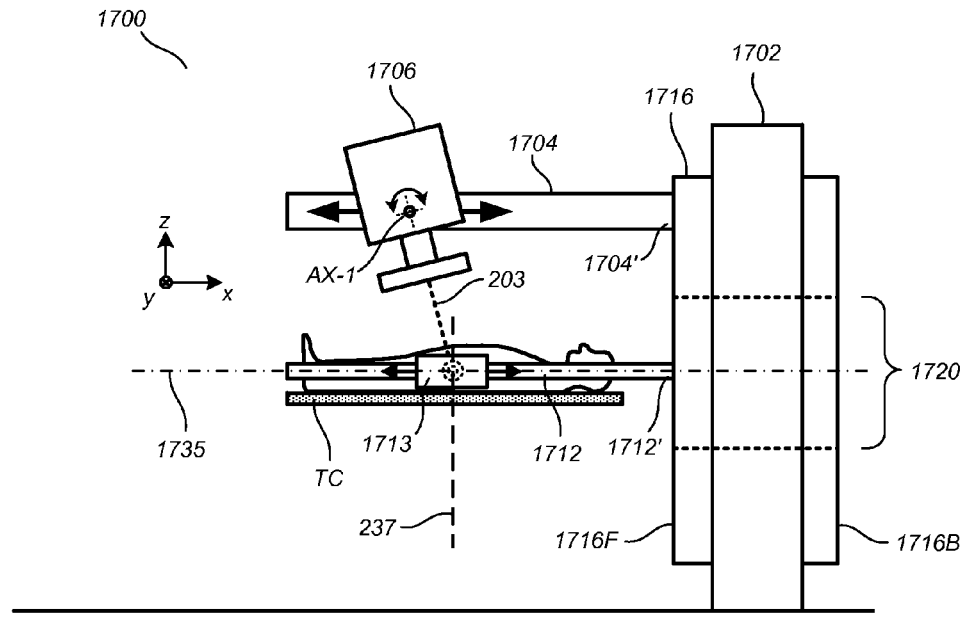
FIG. 17A illustrates a side view of an IGRT apparatus according to a preferred embodiment.

FIG. 17A illustrates a side view of an IGRT system 1700 according to a preferred embodiment. The IGRT system 1700 of FIG. 17A is further illustrated and described with respect to FIG. 17B which shows an endwise cutaway view of the IGRT apparatus 17. IGRT system 1700 comprises a gantry frame 1702 including a first ring member 1716, the first ring member 1716 being rotatable around a substantially horizontal, longitudinally extending central axis 1735. The first ring member 1716 has a first end 1716F and a second end 1716B that horizontally opposes the first end 1716F. The IGRT apparatus 1700 further comprises a radiation treatment head 1706 coupled to the first ring member 1716 in an outwardly movable manner by an arm member 1704 that extends in an outward direction from the first end 1716F of the first ring member 1716 in a direction pointing away from the second end 1716B. The arm member 1704 connects to the first ring member 1716 at an arm member base 1704', which can also be termed a shoulder. The outward movability of the radiation treatment head 1706 is characterized in that the radiation treatment head 1706 is movable in at least a longitudinal direction toward and away from the first end 1716F of the ring member. According to the preferred embodiment of FIGS. 17A-17B, the arm member 1704 is a single continuous beam member that extends outwardly from the first ring member 1716 at a fixed orientation, such as a horizontal orientation, and the radiation treatment head 1706 is longitudinally translatable along the arm member 1704. Preferably, the radiation treatment head 1706 is also pivotable around at least one axis AX-1, whereby noncoplanar radiation treatment can be provided. A kV source-detector pair 1713/1715 (the latter element 1715 being hidden from view in FIG. 17A) is coupled to an independently rotatable second ring member 1718 by respective single continuous beam members 1712 and 1714 that extend outwardly from the second 1718 at fixed orientations, such as horizontal orientations. Each element of the kV source-detector pair 1713/1715 is longitudinally translatable along its respective beam member 1712/1714. Beam members 1712/1714 are connected to the second ring member 1716 at arm member bases (shoulders) 1712'/1714'.

Figure 17B:
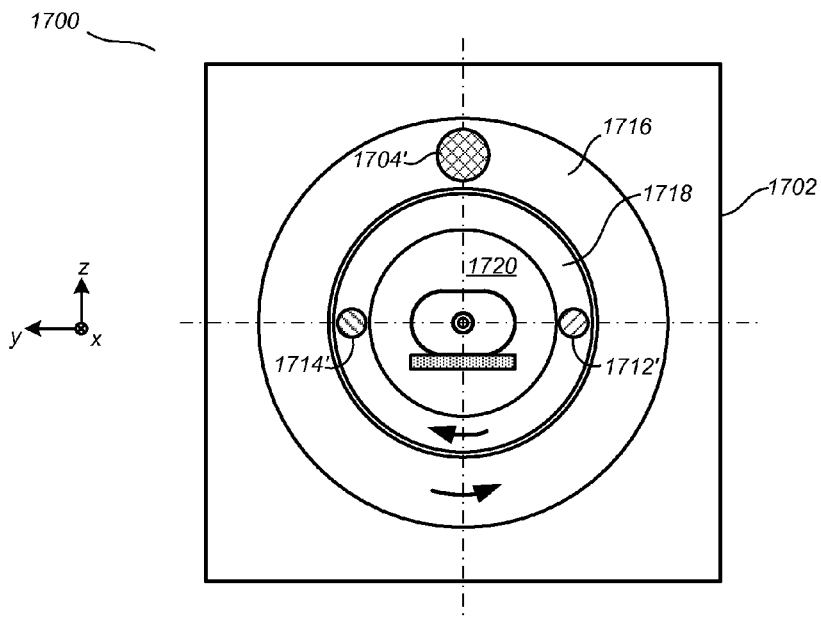
FIG. 17B illustrates an endwise cutaway view of the IGRT apparatus of FIG. 17A.
Figure 18A:
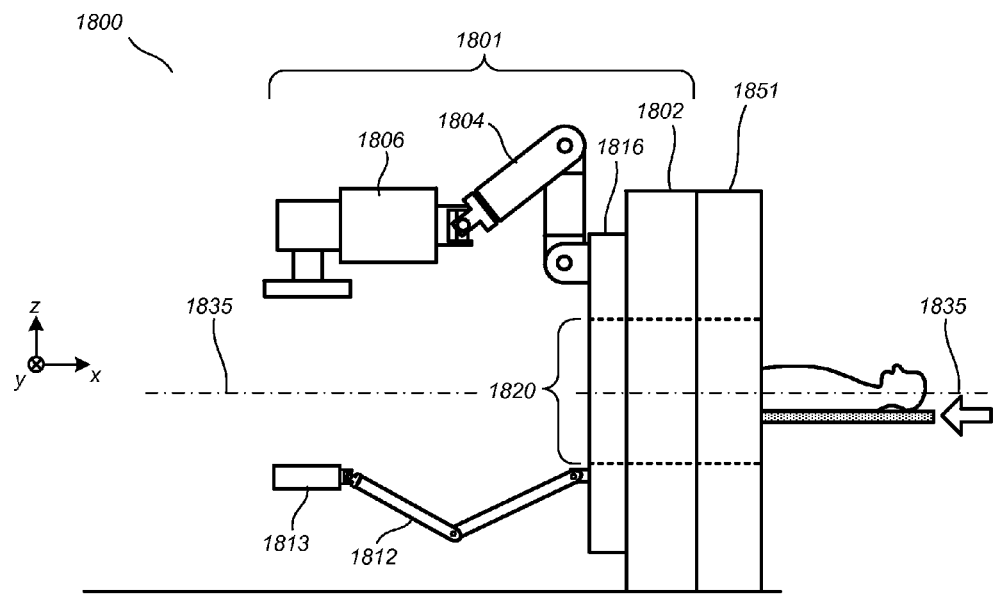
FIGS. 18A-18D illustrate side views of an IGRT apparatus according to a preferred embodiment at successive stages of a high resolution CT imaging process and associated radiation treatment fraction.
Figure 18B:
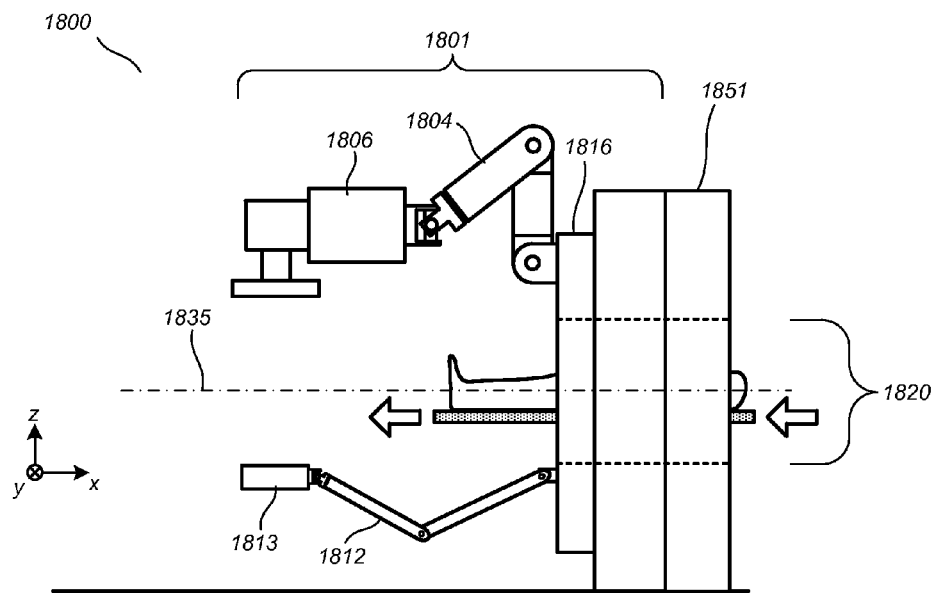
Figure 18C:
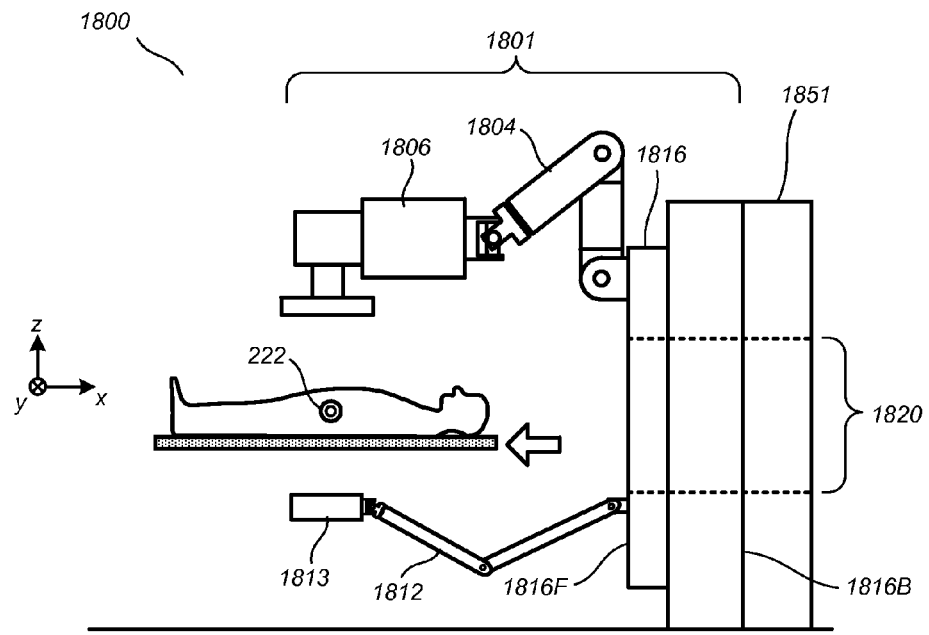
Figure 18D:
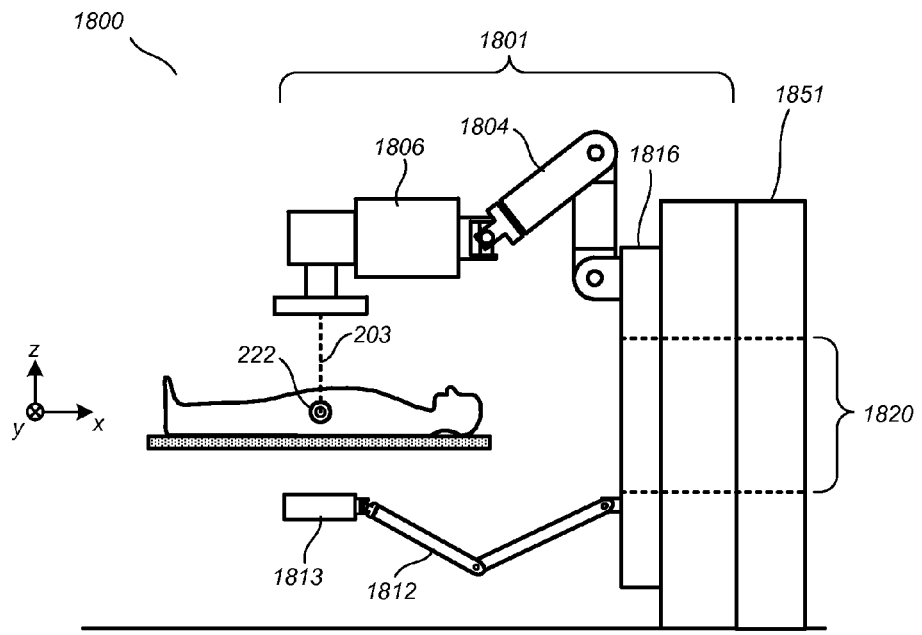

Similar to the preferred embodiment of FIGS. 2A-2B supra, the IGRT system 1700 of FIGS. 17A-17B is characterized in that the arm member 1700 extends outwardly from the first end 1716F of the ring member 1716 in a direction away from the second end 1716B and is supported only at its shoulder member. Also similar to the preferred embodiment of FIGS. 2A-2B supra, the radiation treatment head 1706 is dynamically movable in at least a longitudinal direction toward and away from the ring member 1716.

FIGS. 18A-18D illustrate side views of an IGRT apparatus 1800 according to a preferred embodiment at successive stages of a high resolution CT imaging process and associated subsequent radiation treatment fraction. The IGRT apparatus 1800 comprises a robot-arm-on-gantry-based IGRT system 1801 that is similar to that of the above-described preferred embodiments (more particularly, a portal imaging-based embodiment similar to that of FIG. 13, supra, although any of the above-described preferred embodiments can be used), comprising a gantry frame 1802, ring member 1816, radiation treatment head 1806, portal imager 1813, and articulated robot arms 1804 and 1812. Also provided, however, is a high resolution collimated CT imaging apparatus 1851 disposed adjacent to the gantry frame 1802 on a side opposite the articulated robot arms 1804 and 1812, wherein the CT imaging apparatus 1851 shares a same central axis of rotation 1835 with the ring member 1816 and forms a common central bore 1820 with the ring member 1816. Operating the IGRT apparatus 1800 can comprise translating the patient through the central bore 1820 while operating the CT imaging apparatus 1851 to acquire at least one high resolution three-dimensional CT image of the body part to be treated, and then subsequently using information derived from the at least one high resolution three-dimensional CT image to properly position the patient into a treatment position and/or to guide the application of treatment radiation to the body part during the treatment fraction. Registration of intrafraction images acquired by the onboard imaging hardware of the IGRT system 1801 with the high resolution three-dimensional CT images acquired by the high resolution CT imaging system 1851 can be greatly facilitated by virtue of the integrated/collocated arrangement along a common central axis.

Figure 19:
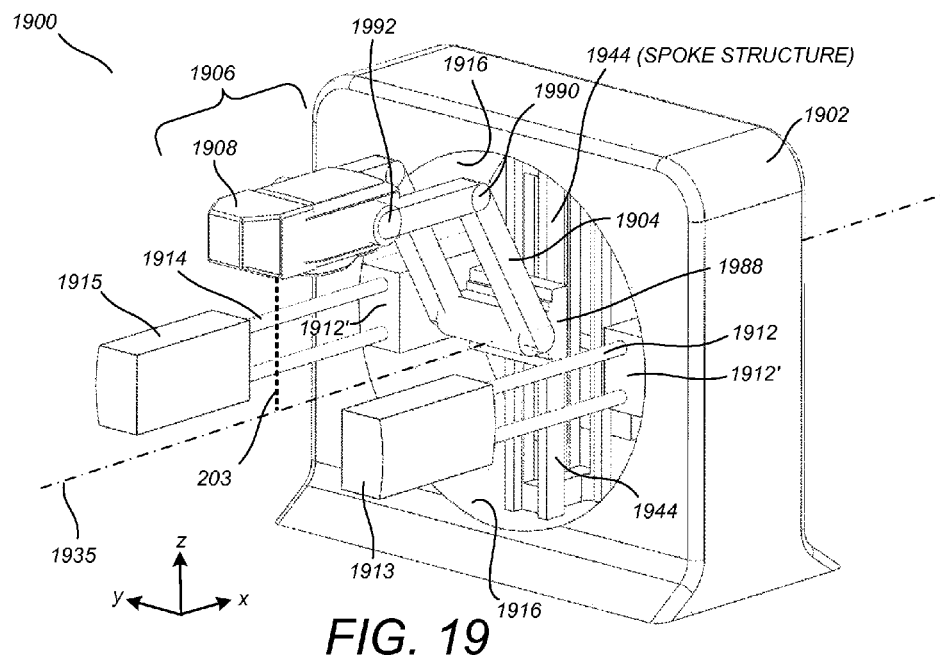
FIG. 19 illustrates a perspective view of an IGRT apparatus according to a preferred embodiment.
Figure 20:
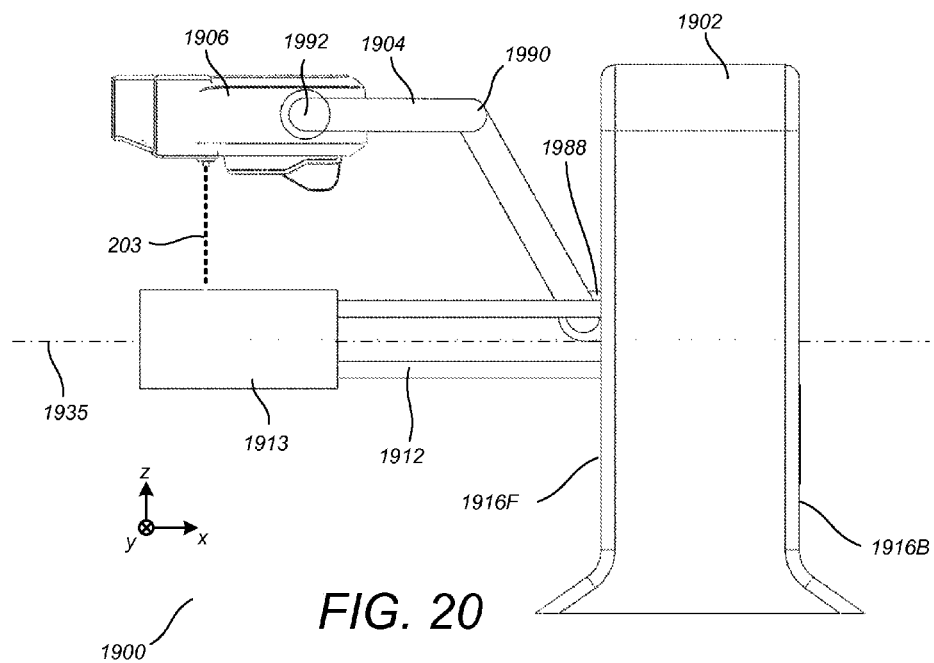
FIG. 20 illustrates a side view of the IGRT apparatus of FIG. 19.
Figure 21:
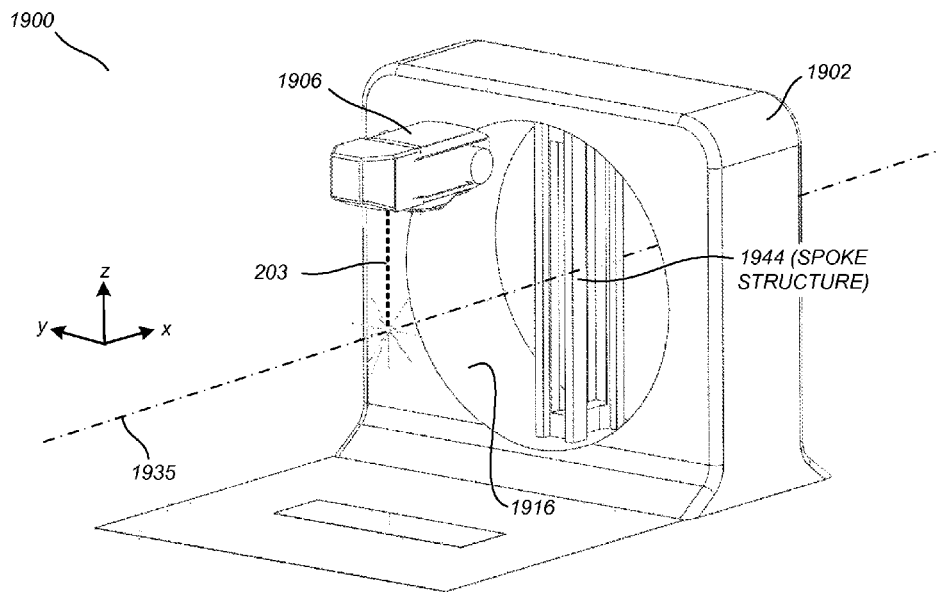
FIGS. 21-24 illustrate perspective views of the IGRT apparatus of FIG. 19 in different treatment positions.
Figure 22:
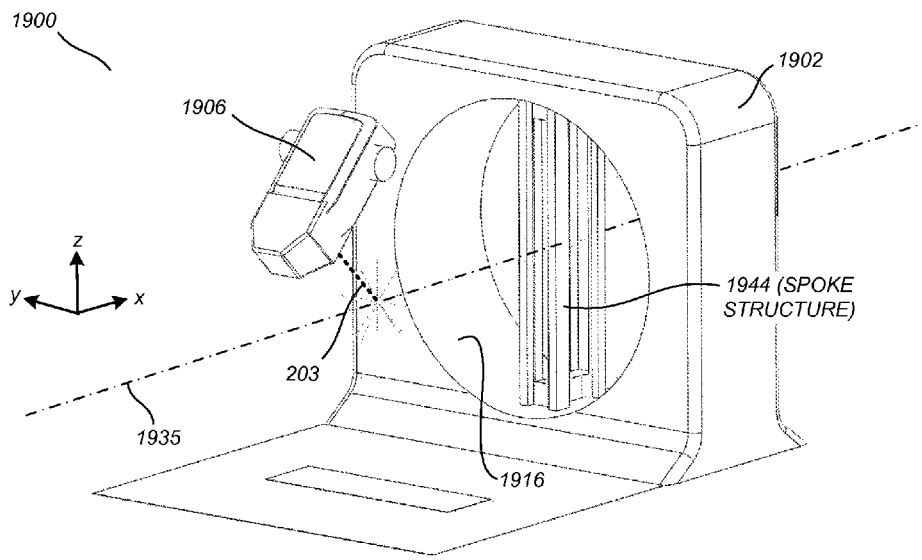
Figure 23:
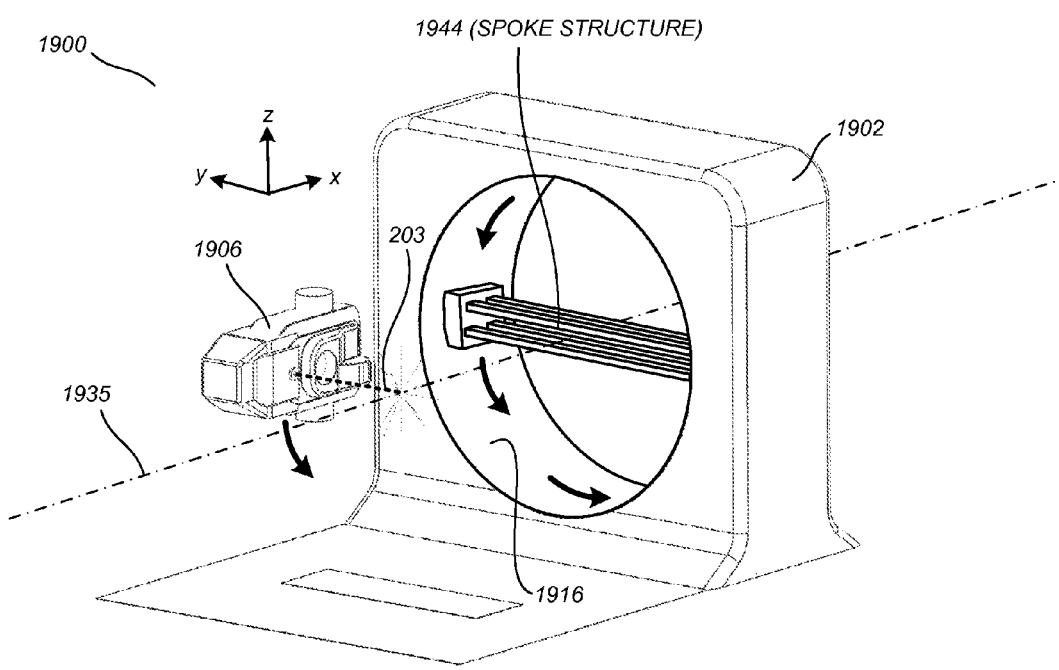
Figure 24:
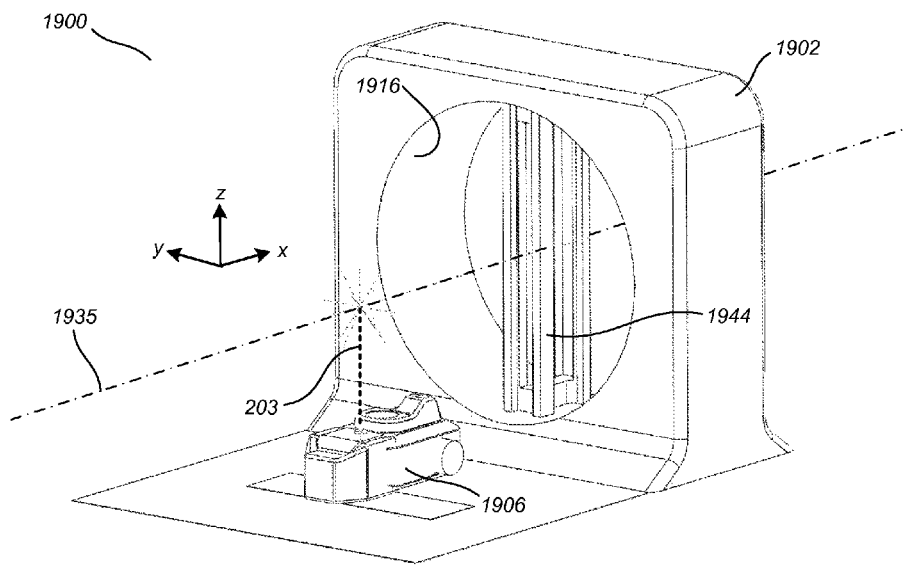
Figure 25:
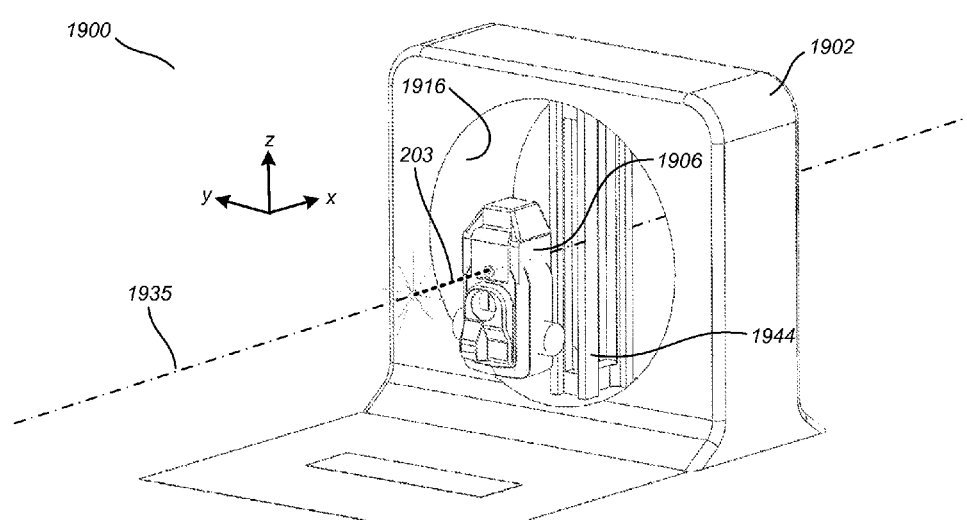
FIG. 25 illustrates a perspective view of the IGRT apparatus of FIG. 19 in an apex cranial treatment position according to a preferred embodiment.

FIG. 19 illustrates a perspective view of an IGRT apparatus 1900 according to a preferred embodiment. FIG. 20 illustrates a side view of the IGRT apparatus 1900 of FIG. 19. IGRT system 1900 comprises a gantry frame 1902 including a ring member 1916 that is rotatable around a substantially horizontal, longitudinally extending central axis 1935. The ring member 1916 has a first end 1916F (see FIG. 20) and second end 1916B (see FIG. 20) that horizontally opposes the first end 1916F. The IGRT apparatus 1900 further comprises a radiation treatment head 1906 coupled to the ring member 1916 in an outwardly movable manner by an articulated robot arm 1904 that extends in an outward direction relative to the ring member 1916. More particularly, there is provided a spoke structure 1944 that is fixably mounted within the ring member 1916 and rotatable therewith around the central axis 1935. The spoke structure 1944 can extend across an inner diameter of the ring member 1916 as shown in the example of FIGS. 19-20, or more generally can be oriented along a secant of the ring member 1916 that passes reasonably close to the center. The articulated robot arm 1904 couples to the ring member 1916 by virtue of a shoulder joint 1988 that is translatably movable along the spoke structure 1944.

A source-axis distance between the radiation treatment head 1906 and the central axis 1935 is dynamically variable by translation of said shoulder joint along the spoke structure 1944. More generally, there are five (5) independently controllable degrees of freedom with which to control the radiation treatment head 1906: rotation of the ring member 1916; translation of the shoulder joint 1988 along the spoke structure 1944; rotation of the shoulder joint 1988; rotation of an elbow joint 1990; and rotation of a single degree-of-freedom wrist joint 1992. Mechanical stability is enhanced by virtue of providing each segment of the articulated robot arm as a dual-beam structure. In alternative preferred embodiments, an additional degree of freedom can be provided by a twisting capability (not shown) at the wrist joint 1992.

The radiation treatment head 1906 includes a bending magnet 1908 to promote outward radial compactness relative to the central axis 1935. Counterweights (not shown), including but not limited to dynamically moving counterweights, are provided on the side of the gantry frame 1902 opposite the radiation treatment head 1906. The IGRT apparatus 1900 further comprises a kV source-detector pair 1913/1915 coupled to the ring member 1916 at base members (shoulder members) 1912'/1914' of arm members 1912/1914. Preferably, the arm members 1912-1914 are retractable in the positive-x direction such that each of the imaging elements 1913/1915 can be retracted back toward and into the gantry frame 1902 when not in use. Advantageously, the radiation treatment head 1906 can also be neatly "folded away" by the robotic arm 1904 to a position close-in to the gantry frame 1902, thereby allowing for more room for other activity and/or equipment in the clinical environment when the IGRT system 1900 is not in use.

FIGS. 21-25 illustrate perspective views of the IGRT apparatus 1900 of FIG. 19 in different treatment positions, with the articulated robot arm 1904 thereof and the kV imaging equipment being omitted from these drawings for clarity of presentation. As illustrated by the orientation of treatment radiation beam 203 in FIG. 22, the IGRT apparatus 1900 is capable of non-coplanar radiation treatment as well as coplanar treatment. The IGRT apparatus 1900 is further capable of accommodating multiple treatment centers at different longitudinal positions along the central axis 1935. As illustrated by the orientation of treatment radiation beam 203 in FIG. 25, the IGRT apparatus 1900 is also capable of providing radiation treatment in an apex cranial orientation.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the embodiments are not intended to limit their scope, which is limited only by the scope of the claims set forth below.

What is claimed is:

1. An image-guided radiation treatment (IGRT) apparatus, comprising:
   a gantry frame including a ring member, the ring member being rotatable around a substantially horizontal, longitudinally extending central axis, said ring member having first and second horizontally opposing ends;
   a radiation treatment head coupled to said ring member in an outwardly movable manner by an arm member extending outwardly from said first end of said ring member in a direction away from said second end, said outward movability being characterized in that said radiation treatment head is movable in at least a longitudinal direction toward and away from said first end of said ring member; and
   a spoke structure fixably mounted within the ring member and rotatable therewith around the central axis, wherein said arm member couples to said ring member at a shoulder joint that is translatably movable along said spoke structure, whereby a source-axis distance between the radiation treatment head and the central axis is dynamically variable by translation of said shoulder joint along said spoke structure.

2. The IGRT apparatus of claim 1, said IGRT apparatus accommodating a treatment center at any of a plurality of longitudinal locations along the central axis by virtue of said longitudinal movability of the radiation treatment head, wherein said radiation treatment head is dynamically tiltable relative to a transverse treatment center plane for any of said longitudinal treatment center locations, whereby said IGRT apparatus is capable of noncoplanar radiation treatment for any of said longitudinal treatment center locations.

3. The IGRT apparatus of claim 2, wherein said arm member comprises an articulated robot arm including said shoulder joint, said radiation treatment head being coupled to said articulated robot arm at a distal end thereof opposite said shoulder joint.

4. The IGRT apparatus of claim 3, wherein said articulated robot arm includes a first arm segment coupled between said shoulder joint and an elbow joint and a second arm segment coupled between said elbow joint and a three degree-of-freedom wrist member, said radiation treatment head being coupled to and supported by said wrist member.

5. The IGRT apparatus of claim 3, wherein said articulated robot arm is configured such that said radiation treatment head is dynamically movable into an apex treatment position in which a radiation treatment beam emanates therefrom at or near the central axis and is substantially parallel to the central axis.

6. The IGRT apparatus of claim 2, wherein said radiation treatment head is dynamically tiltable along at least two tilt axes for any of said longitudinal treatment center locations, whereby said IGRT apparatus is further capable of accommodating off-central-axis treatment centers for any of said longitudinal treatment center locations.

7. The IGRT apparatus of claim 1, said arm member being a first arm member, the IGRT apparatus further comprising:
   a kV imaging source coupled to said gantry frame in an outwardly movable manner by a second arm member extending outwardly from said gantry frame on a same side thereof as said radiation treatment head; and
   a kV imaging detector coupled to said gantry frame in an outwardly movable manner by a third arm member extending outwardly from said gantry frame on said same side as said radiation treatment head, said kV imaging detector being disposed generally opposite said kV imaging source relative to said central axis.

8. The IGRT apparatus of claim 7, said second and third arm members comprising respective articulated robot arms having respective shoulder joints connected to said gantry frame, said kV imaging source and kV imaging detector being coupled to said second and third arm members, respectively, at respective distal ends thereof opposite said respective shoulder joints thereof.

9. The IGRT apparatus of claim 7, wherein said second and third arm members are coupled to said ring member such that said kV imaging source and said kV imaging detector rotate in unison with said radiation treatment head around said central axis.

10. The IGRT apparatus of claim 7, said kV imaging source and said kV imaging detector forming a first kV imaging source-detector pair, said IGRT apparatus further comprising a second kV imaging source-detector pair coupled to said gantry frame in an outwardly movable manner by fourth and fifth arm members, respectively, said first and second kV imaging source-detector pairs being mutually positioned in a stereoscopic imaging configuration around said central axis.

11. The IGRT apparatus of claim 10, said second, third, fourth, and fifth arm members comprising respective articulated robot arms having respective shoulder joints connected to said gantry frame, said first and second kV imaging sources and first and second kV imaging detectors being coupled to second, third, fourth, and fifth arm members, respectively, at respective distal ends thereof opposite said respective shoulder joints thereof.

12. The IGRT apparatus of claim 10, wherein said second, third, fourth, and fifth arm members are coupled to said ring member such that said first and second kV imaging source-detector pairs rotate in unison with said radiation treatment head around said central axis.

13. The IGRT apparatus of claim 1, wherein said arm member comprises an articulated robot arm including a first arm segment coupled between said shoulder joint and an elbow joint and a second arm segment coupled between said elbow joint and an at least one degree of freedom wrist joint, said radiation treatment head being coupled to and supported by said wrist joint.

14. The IGRT apparatus of claim 13, wherein said radiation treatment head is a LINAC including one of a 90-degree and 270-degree bending magnet for promoting physical compactness thereof in a radial dimension around the central axis.

15. An image-guided radiation treatment (IGRT) apparatus, comprising:
   a gantry frame including a ring member, the ring member being rotatable around a substantially horizontal, longitudinally extending central axis, said ring member having first and second horizontally opposing ends; and
   a radiation treatment head coupled to said ring member by an arm member, said arm member being connected to said ring member at an arm member;
   a spoke structure fixably mounted within the ring member and rotatable therewith around the central axis, wherein said arm member couples to said ring member at said arm member base which is translatably movable along said spoke structure, whereby a source-axis distance between the radiation treatment head and the central axis is dynamically variable by translation of said shoulder joint along said spoke structure;
   wherein:
      said arm member extends outwardly from said first end of said ring member in a direction away from said second end and is supported only by said arm member base; and
      said radiation treatment head is dynamically movable in at least a longitudinal direction toward and away from said first end of said ring member.

16. The IGRT apparatus of claim 15, said IGRT apparatus accommodating a treatment center at any of a plurality of longitudinal locations along the central axis by virtue of said longitudinal movability of the radiation treatment head, wherein said radiation treatment head is dynamically tiltable relative to a transverse treatment center plane for any of said longitudinal treatment center locations, whereby said IGRT apparatus is capable of noncoplanar radiation treatment for any of said longitudinal treatment center locations.

17. The IGRT apparatus of claim 16, wherein said arm member comprises an articulated robot arm including said arm member base, said radiation treatment head being coupled to said articulated robot arm at a distal end thereof opposite said shoulder joint.

18. The IGRT apparatus of claim 17, wherein said articulated robot arm includes a first arm segment coupled between said arm base member and an elbow joint and a second arm segment coupled between said elbow joint and a three degree-of-freedom wrist member, said radiation treatment head being coupled to and supported by said wrist member.

19. The IGRT apparatus of claim 15, said arm member being a first arm member, the IGRT apparatus further comprising:
   a kV imaging source coupled to said gantry frame in an outwardly movable manner by a second arm member extending outwardly from said gantry frame on a same side thereof as said radiation treatment head; and
   a kV imaging detector coupled to said gantry frame in an outwardly movable manner by a third arm member extending outwardly from said gantry frame on said same side as said radiation treatment head, said kV imaging detector being disposed generally opposite said kV imaging source relative to said central axis.

20. The IGRT apparatus of claim 19, said second and third arm members comprising respective articulated robot arms having respective shoulder joints connected to said gantry frame, said kV imaging source and kV imaging detector being coupled to said second and third arm members, respectively, at respective distal ends thereof opposite said respective shoulder joints thereof.

21. The IGRT apparatus of claim 20, wherein said second and third arm members are coupled to said ring member such that said kV imaging source and said kV imaging detector rotate in unison with said radiation treatment head around said central axis.

* * * * *